United States Patent [19]

Bell

[11] Patent Number: 4,653,539
[45] Date of Patent: Mar. 31, 1987

[54] SELF-SEALING CHECK VALVE
[75] Inventor: Craig J. Bell, Lake George, N.Y.
[73] Assignee: Mallinckrodt, Inc., St. Louis, Mo.
[21] Appl. No.: 619,933
[22] Filed: Jun. 12, 1984
[51] Int. Cl.⁴ .................................................. F16K 15/14
[52] U.S. Cl. ..................................... 137/860; 137/843; 128/207.15; 604/99
[58] Field of Search ............... 137/843, 852, 853, 860; 251/149.1, 149.7, 149.8; 128/207.15; 604/97, 98, 99, 247

[56] References Cited
U.S. PATENT DOCUMENTS

| | | | |
|---|---|---|---|
| 2,912,981 | 11/1959 | Keough | 604/98 |
| 2,993,654 | 7/1961 | Norton | 137/853 |
| 3,346,001 | 10/1967 | Camp | 137/852 |
| 3,416,567 | 12/1968 | Von Dardel et al. | 604/83 |
| 3,794,043 | 2/1974 | McGinnis | 251/149 |
| 3,831,629 | 8/1974 | Mackal et al. | 251/149.7 |
| 4,063,555 | 12/1977 | Ulinder | 604/83 |
| 4,143,853 | 3/1979 | Abramson | 251/149.1 |
| 4,171,007 | 10/1979 | Bouteille | 137/853 |
| 4,489,750 | 12/1984 | Nehring | 137/853 |

Primary Examiner—Martin P. Schwadron
Assistant Examiner—Sheri M. Novack
Attorney, Agent, or Firm—Bernard, Rothwell & Brown

[57] ABSTRACT

A self-sealing check valve is disclosed for use in the inflation of a catheter cuff. The valve includes a valve housing and a valve element sealingly positioned within the housing. The valve housing has a transversely located fitting for receiving a Luer tip device. A valve element is cylindrical and preferably hollow. A circumferential rim at each end of the element is maintained in a state of compression so that it presses against the inner wall of the housing to form a seal. The element also includes a circumferential channel which is aligned with the Luer fitting. Insertion of the Luer tip device into the fitting depresses the valve element and breaks the seal between the rims and the valve housing wall. This allows fluid flow in either direction through the valve. Resiliency of the valve element causes resealment at the rims when the Luer tip device is removed.

5 Claims, 4 Drawing Figures

SELF-SEALING CHECK VALVE

BACKGROUND OF THE INVENTION

1. Field of the Invention

This invention is concerned with improvements in check valves, and more particularly is directed to the class of such valves having a self-sealing feature. The invention is meant primarily for use in catheters and similar medical applications involving the transport of fluids.

2. Description of the Prior Art

Catheters are frequently used in medical applications for conducting fluids to or from body cavities. In many cases catheters are provided with a cuff (inflatable balloon), suitable for engaging and sealing the wall of a body passage so as to limit passage of fluid to or from the body cavity to that passing through the catheter. For example, a tracheal catheter may be designed for insertion into the trachea and may include an inflatable balloon near the distal end for sealing the tracheal passage. It is important that the balloon be easily inflated and that it remain in the inflated condition for the desired length of time. For example, a tracheal catheter may be employed in connection with a surgical procedure extending over a significant period of time, and it is necessary that the balloon remain reliably inflated throughout this time. For this purpose it is conventional to provide a check valve in a tube connected to the balloon for inflation thereof. It is desirable that this check valve, which in this specification will hereinafter also be referred to as an inflation valve, be easily actuated when it is desired to supply fluid to the aforementioned balloon of the catheter or when it is desired to discharge the fluid therefrom, and it is desirable that the valve remain reliably sealed during the intervening period.

It is increasingly common that catheters of this type are intended to be disposable after a single use. Accordingly, it is desirable that such devices be of simple construction and inexpensive to manufacture. These requirements, of course, apply to the inflation valve which forms part of the disposable catheter. Many prior art inflation valves have three or more parts and have involved significant cost in manufacture and assembly. The prior art does include some two-piece inflation valves but these prior art two-piece valves have involved additional manufacturing operations or assembly problems which increase the cost and make them less desirable, therefore, for use as disposable items.

The valve of the present invention differs from those of the prior art in that it employs a highly simplified two-piece construction. This facilitates manufacture of the valve components and reduces manufacturing costs. The structure is such that a valve element seals firmly against a valve housing, insuring against undesired leakage of fluid therethrough, but the element is easily moved away from the housing, when desired, to interrupt the seal and allow the free flow of fluids through the valve in either direction.

SUMMARY OF THE INVENTION

The self-sealing check valve of this invention, in one form thereof, comprises a hollow valve housing formed of a rigid or semi-rigid material, having an open end and a closed end, and further having an inner wall providing a longitudinal passage between the open and closed ends. The valve housing includes a fitting extending transversely from one wall thereof and communicating with the passage. The fitting is capable of accepting a Luer tip device. A valve element formed of resilient material is received within the passage. The element includes a circumferential rim at each end which sealingly engages the inner wall of the housing. The valve element further includes a channel extending circumferentially thereof and aligned with the fitting. The element can be engaged by a Luer tip device and is moveable thereby inwardly to displace the circumferential rims of the element from the inner wall, permitting passage of fluid therebetween. The valve element, because of its resiliency, resumes its normal position when the Luer tip device is removed and thereby resumes sealing engagement with the inner wall.

DESCRIPTION OF THE PREFERRED EMBODIMENTS

Figure 1:
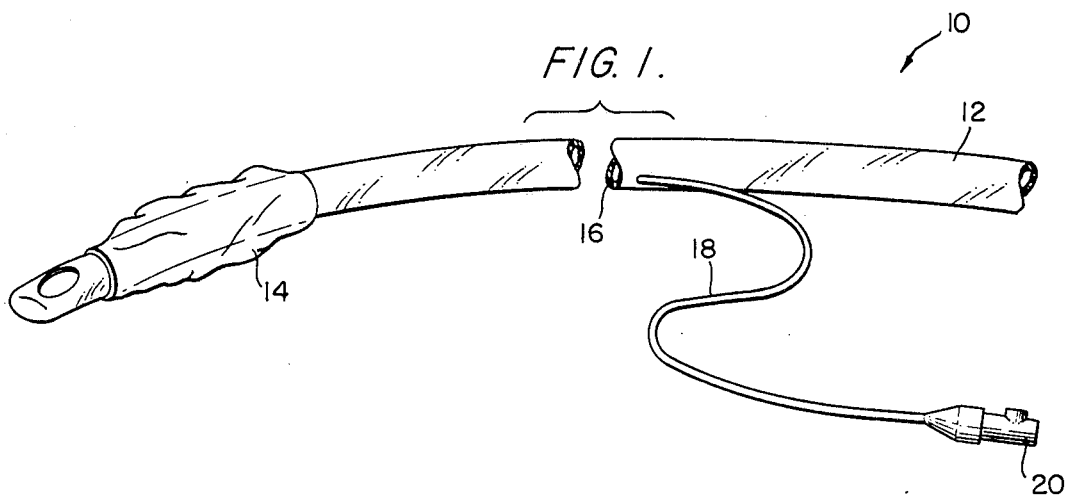
FIG. 1 is a general view of a catheter incorporating the valve of this invention.

Referring to FIG. 1, there is shown a general representation of a catheter 10 which includes a tube 12 for passage of fluids to and from a body cavity. The catheter includes an inflatable cuff 14 at its distal end. A secondary lumen 16 is formed within the wall of the tube 12. The distal end of the lumen 16 communicates with the interior of the cuff, while the proximal end connects to a tube 18 for passage of fluid to inflate or deflate the cuff. A valve 20, constructed in accordance with this invention, is shown connected to the proximal end of tube 18 for controlling passage of fluid through the lumen 16.

Figure 2:
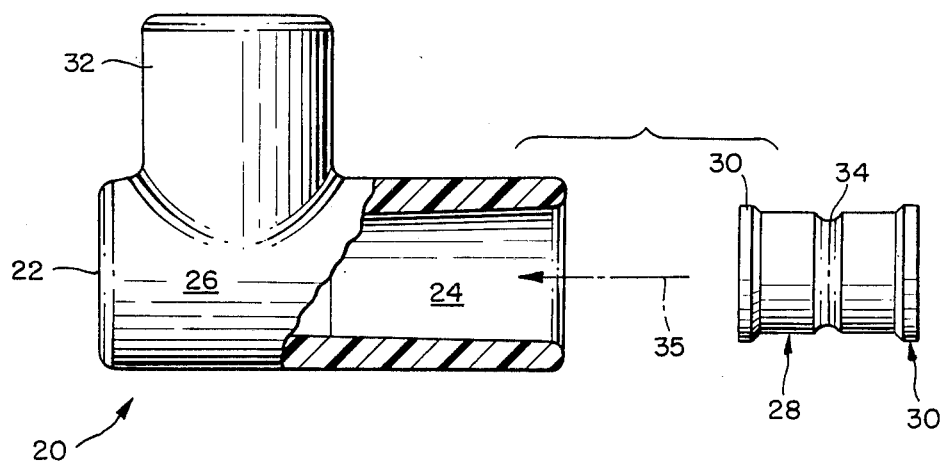
FIG. 2 is a side view, partly in section, of a valve element and housing illustrating the method of assembly.
Figure 3:
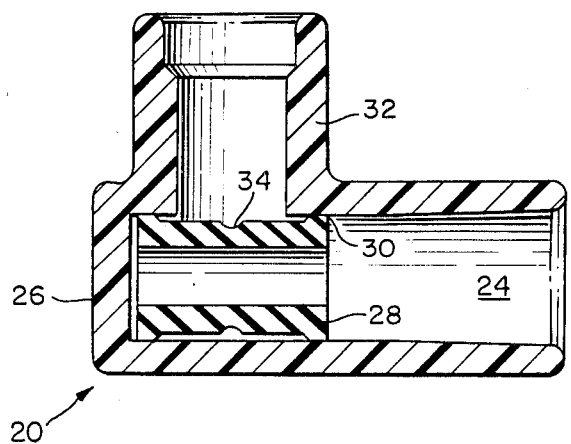
FIG. 3 is a cross-sectional view of the valve in its sealing position.

Turning to FIGS. 2 and 3, the valve 20 comprises a hollow valve housing 22 having open and closed ends 24 and 26 respectively, and a resilient valve element 28 positioned within the housing. Circumferential rims 30 at both ends of element 28 are maintained in a state of compression against the inner surface of the housing to form a seal. Both the housing and the element are preferably cylindrical in shape, this configuration providing the best fit between rims 30 and the inner wall of the housing. Also, the cylindrical shape takes full advantage of the resiliency of the element to uniformly distribute the compressive force along the rims 30. As a result, there is no gap between the rims and the housing which would result in leakage.

The housing includes a fitting 32 capable of accepting Luer tip devices. This fitting is located transversely on the housing outer surface and offset towards the closed end 26 of the valve housing. The fitting 32 extends completely through the valve housing wall, exposing the valve element. The element includes a channel 34 aligned with the fitting 32. This channel is preferably circumferential so that no orientation is required when the valve is assembled. The reason for providing the channel 34 is to ensure that engagement of a Luer tip device through fitting 32 does not result in a seal between the device and the element 28, since this would prevent passage of fluid through the valve. Channel 34 thus has a depth and width sufficient to allow relatively unimpeded flow between the Luer tip and open end 24 of the valve body.

Assembly is easily effected by inserting element 28 through open end 24 of the valve housing, as indicated by arrow 35 in FIG. 2. The housing can advantageously have a slight taper to facilitate insertion of the valve element, such that the inner diameter of the housing at the open end 24 is slightly enlarged.

Figure 4:
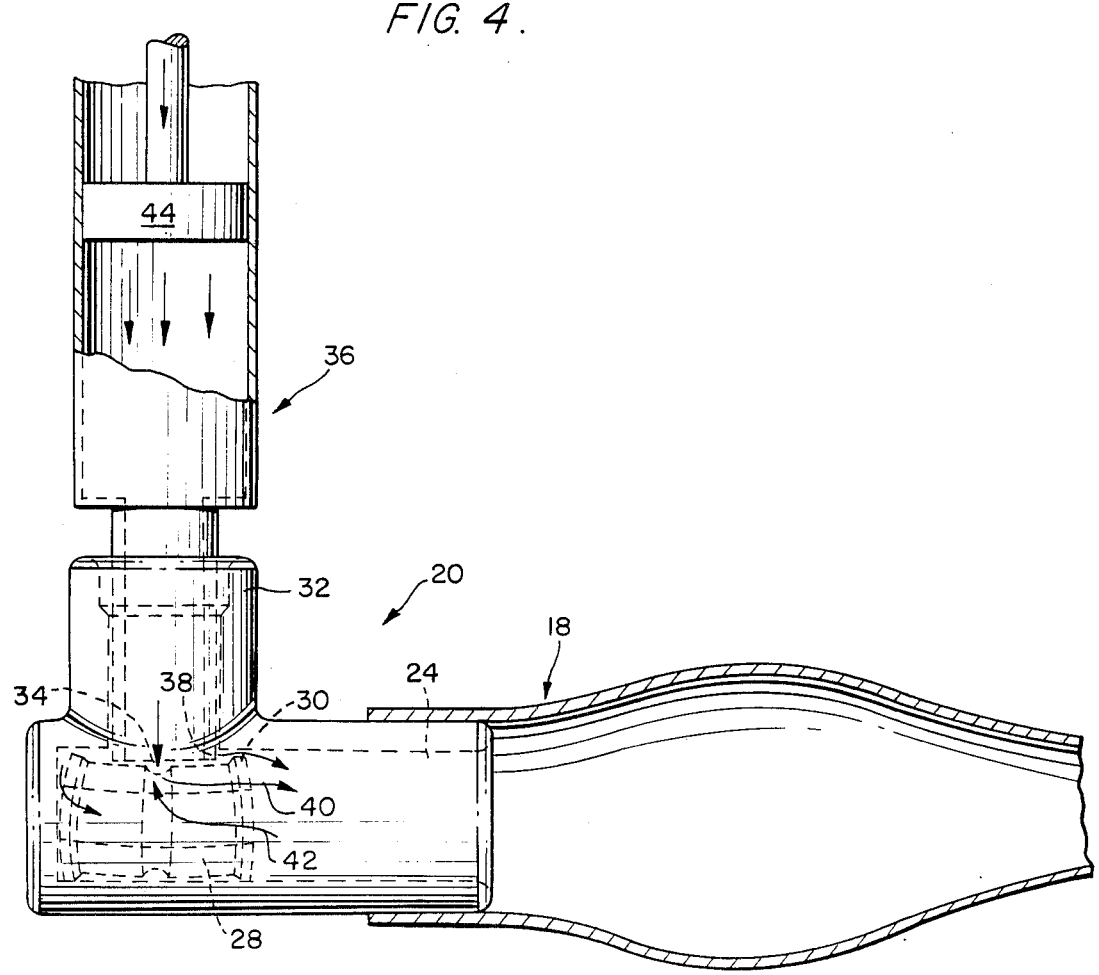
FIG. 4 is a side view of the valve with a Luer tip inserted.

Engagement of a Luer tip syringe 36 can be seen in FIG. 4. A tip 38 of the syringe presses against the surface of the element 28, forcing it inward and resulting in disengagement of the upper portions of the rims 30 from the inner surface of the valve housing. This breaks the seal and permits fluid flow through the valve via the channel 34. The fluid flow can be in either direction as indicated by arrows 40 and 42. A plunger 44 or other suitable mechanism can be used to inject or withdraw fluid.

Thus, for example, a cuff can be inflated or deflated with a Luer tip syringe by connecting the open end 24 of the valve housing to a tube 18. It will be appreciated that the valve element 28 need only be depressed to a degree which allows free flow of fluid. Those skilled in the art can readily ascertain the optimum dimensions of the element 28 and channel 34 based on the type of syringe or other Luer tip device used with the valve. Disengagement and removal of the syringe results in resealment along the rims 30 as the valve element returns to its normal position due to its resilience.

The valve element is preferably an elastomer which can be placed in compression when installed in the valve housing. While the element can be of solid construction, it is preferably tubular, that is, hollow and shaped somewhat like a section of open-ended tubing. The tubular construction has been found to provide substantial compression strength to maintain the seal along the rims 30 and to anchor the element. Yet, this construction allows deformation of the element upon insertion of a syringe into the fitting as outlined above. It also facilitates insertion of the valve element within the valve housing.

The dimensions of the valve housing and the valve element can be varied depending on the intended use. The valve housing is preferably constructed of a rigid or semi-rigid plastic material, such as polyvinyl chloride (PVC), acrylonitrile-butadiene-styrene (ABS), polyethylene, polypropylene or polycarbonate. The valve element is preferably made of an elastomer such as natural rubber (cis 1,4-polyisoprene), which may of course be combined with well known compounding ingredients and cured. Other suitable elastomers include silicone and neoprene as well as the various thermoplastic elastomers. The selection of the material for the element affects the sealing and resealing characteristics of the valve, as does the element design. Those skilled in the art can make a material and design selection appropriate to the intended application. Regardless of the design specifics, however, the valve element and the valve housing are easily manufactured with conventional apparatus.

The valve of the invention has a number of advantages over prior art valves. Because the seal is effected by a resilient valve element, close tolerances on molded pieces are not required, and thus manufacture and assembly of the valve do not require tight controls, which are expensive. Furthermore, rotational force applied to the element will not cause the valve to stick in the open position.

While a specific construction of the check valve of this invention has been illustrated and described, it is not intended that the invention be limited to the particular details of construction shown and described.

I claim:
1. A self-sealing valve comprising:
   (a) a hollow valve housing formed of a rigid or semi-rigid material, having an open end and a closed end, and further having an inner wall providing a longitudinal passage between said open end and said closed end;
   (b) said valve housing including a fitting extending transversely from one wall thereof and communicating with the said passage, said fitting capable of accepting a Luer tip device;
   (c) a valve element formed of resilient material and received within said passage, said element including a circumferential rim at each end thereof which sealingly engages the inner wall of said housing;
   (d) said valve element further including a channel extending circumferentially thereof and aligned with said fitting;
   (e) said element being engageable by a Luer tip device in the region of said channel and being moveable thereby inwardly to displace said circumferential rims of said valve element from said inner wall permitting passage of fluid between said valve element and said inner wall;
   (f) said channel having a depth and width sufficient to allow relatively unimpeded flow of fluid to and from the Luer tip device; and
   (g) said valve element resuming its normal position by the resiliency thereof when the Luer tip device is removed to cause said valve element to resume sealing engagement with said inner wall.

2. A valve as in claim 1, wherein said valve housing and said valve element are cylindrical.

3. A valve as in claim 2, wherein said valve element is hollow and is formed of an elastomeric material.

4. A valve as in claim 3, wherein said valve housing is of a material selected from the group consisting of rigid or semi-rigid polyvinyl chloride, acrylonitrile-butadiene-styrene, polyethylene, polypropylene and polycarbonate.

5. A valve as in claim 4 wherein said valve element is of a material selected from the group consisting of neoprene, natural rubber, thermoplastic elastomer and silicone.

* * * * *